United States Patent [19]

Herzon

[11] Patent Number: 4,962,766
[45] Date of Patent: Oct. 16, 1990

[54] NERVE LOCATOR AND STIMULATOR

[76] Inventor: Garrett D. Herzon, 1730 North Clark St., Apartment 3907, Chicago, Ill. 60614

[21] Appl. No.: 381,811

[22] Filed: Jul. 19, 1989

[51] Int. Cl.$^5$ .................... A61H 39/02; A61N 1/36
[52] U.S. Cl. .................... 128/741; 128/421; 128/801
[58] Field of Search ............ 128/741, 784, 800, 801, 128/421

[56] References Cited

U.S. PATENT DOCUMENTS

| | | |
|---|---|---|
| 1,158,473 | 11/1915 | Floyd . |
| 1,548,184 | 8/1925 | Cameron . |
| 2,437,697 | 3/1948 | Kalom . |
| 2,516,882 | 8/1950 | Kalom . |
| 2,704,064 | 3/1955 | Fizzell et al. . |
| 3,027,891 | 4/1962 | Fields . |
| 3,128,759 | 4/1964 | Bellis . |
| 3,207,151 | 9/1965 | Takagi . |
| 3,364,929 | 1/1968 | Ide et al. ............ 128/741 X |
| 3,664,329 | 5/1972 | Naylor . |
| 3,830,226 | 8/1974 | Staub . |
| 4,100,505 | 7/1978 | Belt et al. . |
| 4,191,188 | 3/1980 | Belt et al. . |
| 4,515,168 | 5/1985 | Chester et al. ............ 128/741 |

FOREIGN PATENT DOCUMENTS 2586552  3/1987  France ............ 128/741

Primary Examiner—Lee S. Cohen
Attorney, Agent, or Firm—Hill, Van Santen, Steadman & Simpson

[57] ABSTRACT

A nerve locator and stimulator which can be used, for example, for human surgery which allows a probe having an insulated tip with an extendible contact which can be used to contact surgical tissue so as to locate a nerve. A second contact is provided with an atraumatic grounding pad and the two contacts are connected to a handpiece which provides an AC energizing current which can be adjusted to fast and low frequency rates. High and low currents can be selected for muscle or nerve simulation and the use of short duration square wave pulses and constant current prevents nerve electrical trauma and neuropraxia or iatrogenic nerve fatigue.

2 Claims, 2 Drawing Sheets

NERVE LOCATOR AND STIMULATOR

BACKGROUND OF THE INVENTION

1. Field of the Invention

This invention relates in general to a novel nerve locator and stimulator.

2. Description of Related Art

U.S. Pat. Nos. 3,664,329, 3,830,226, 3,128,759, 3,027,891, 2,949,407, 2,516,882, 3,207,151, 1,158,473, 2,437,697, 158,184, 2,704,064, 4,191,188 and 4,100,505 disclose apparatus that can be used as nerve stimulators.

Prior art devices do not allow the pulse rate to be selected as in the present invention. Prior art devices use a needle for grounding which is easily pulled out of the patient during use requiring re-insertion of the needle.

SUMMARY OF THE INVENTION

The present invention provides a nerve locator and stimulator comprising a handpiece with an insulated tip that allows accurate delivery of current to a deep nerve without shunting on overhanging tissue. The invention allows high or low constant current to be selected for muscle or nerve stimulation. The invention also has a frequency switch with fast and slow rates to allow use of the stimulator with sensory alarms.

The present invention relates to an improved nerve locator and stimulator which provides a high degree of accuracy for the surgeon and allows the frequency and amplitude of the current to be selected which gives broad flexibility. Both visible and auditory signals are supplied to the surgeon during operation.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DESCRIPTION OF THE PREFERRED EMBODIMENTS

Figure 1:
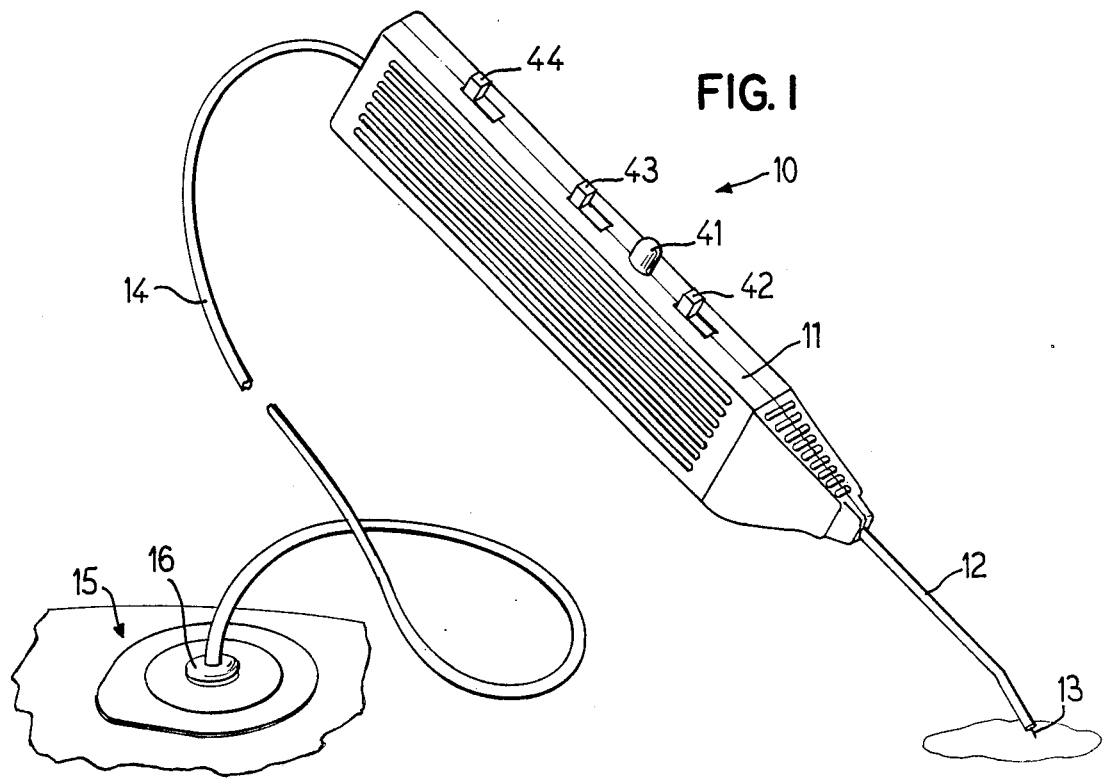
FIG. 1 is a perspective view of the improved nerve locator and stimulator of the invention.
Figure 2:
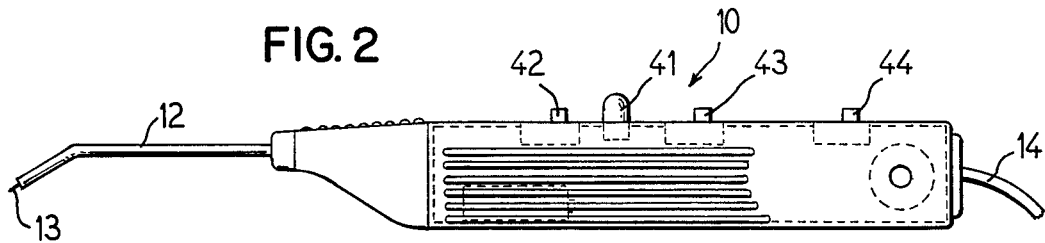
FIG. 2 is a side plan view of the invention.
Figure 3:
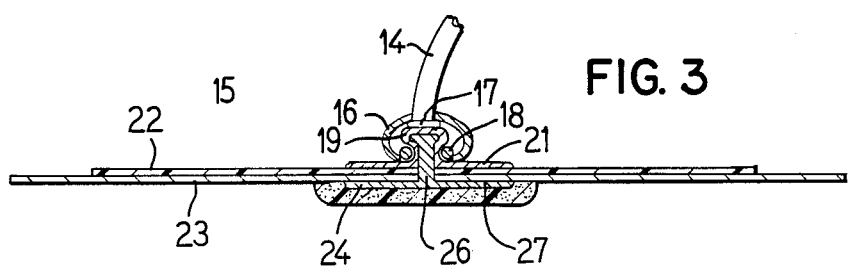
FIG. 3 is a detail view illustrating the means of making an electrical contact remote from the operating site.

The nerve locator and stimulator 10 illustrated in FIGS. 1, 2 and 3 comprises a handpiece 11 which has a probe which extends from one end comprising an insulating sleeve 12 and an electrical contact 13 which engages nerves or muscles of the patient. A lead 14 extends from the other end of the handpiece 11 and terminates in a connector 16 which is connected to a monitoring electrode 15. The monitoring electrode 15 is a commercially available element available from the Medical-surgical Division of the 3M Company and is shown in detail in FIG. 3. It comprises a plastic layer 23 which carries an adhesive for sticking and holding an electrical contacting pad 24 to the skin of a patient. An electrical contact 27 has a disk-shaped portion and has a shank 26 which extends through the plastic layer 23. A plastic portion 22 is attached to the plastic portion 23 and the shank 26 extends therethrough. A contact 19 engages the shank 26 and has a disk-shaped portion 21 which lies against the plastic portion 22. The conductor 14 has an end contact 17 which engages the contact 19 of the contact member 21 when a holding member 16 which includes a ring-shaped member 18 is inserted over the head 19 and electrical contact occurs between member 19 and member 17. Since the member 19 is electrically connected through the shank 26 to the pad 24 which makes electrical contact with the skin of the patient, electrical contact is made between the lead 14 and the skin of the patient.

The handpiece 10 has an indicator light 41 and on and off switch 43, a high and low constant current switch 44 and a pulse speed switch 42.

Figure 4:
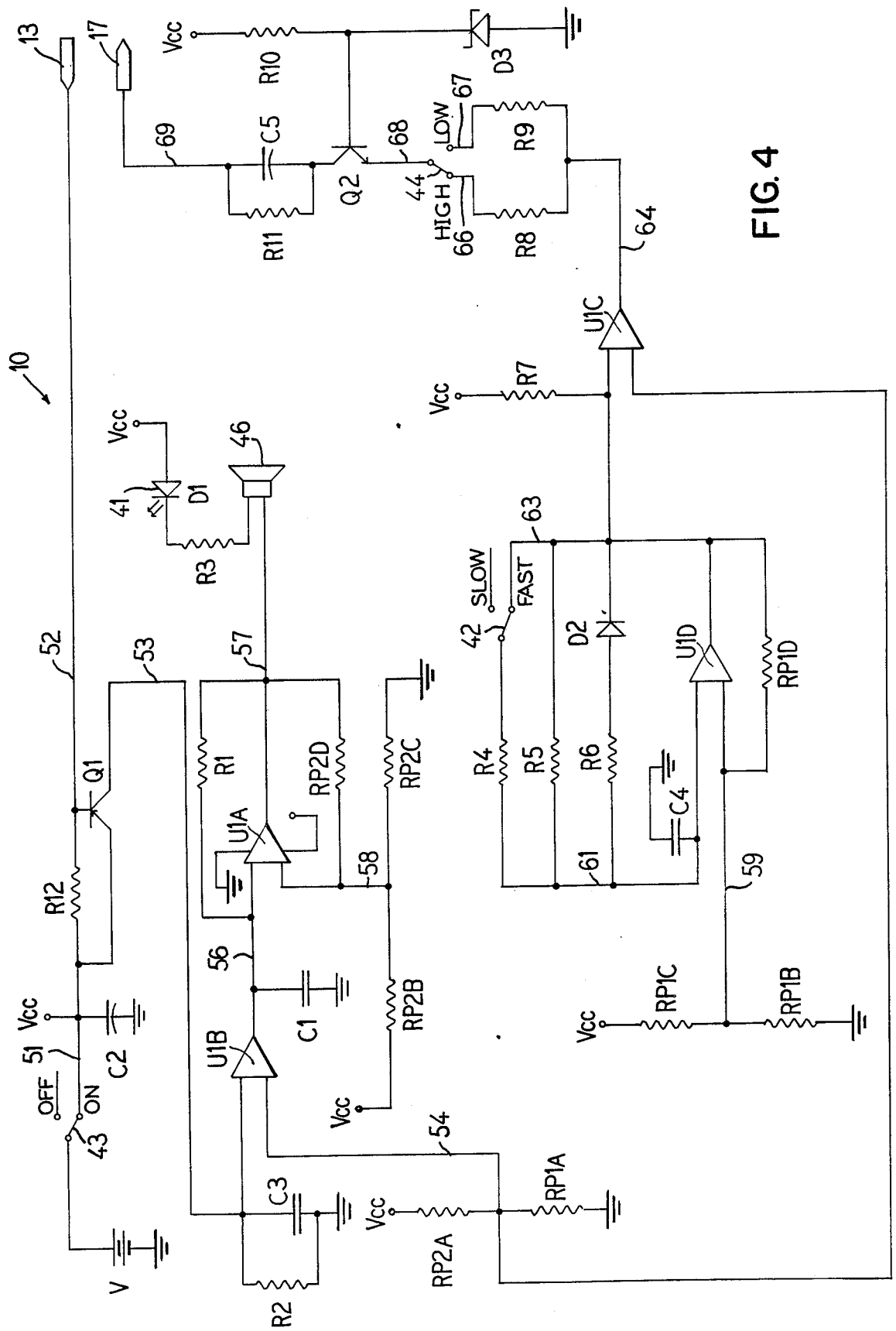
FIG. 4 is an electrical schematic of the invention.

FIG. 4 is an electrical schematic of the invention. A voltage source V which might be a 12 volt battery is connected to the on/off switch 43 which can be moved between on and off positions. When in the on-position, it engages lead 51 which is connected to ground through capacitor C2 which might be 1.0 microfarad. Lead 51 is connected to resistor R12 which might be 4.7K and to the emitter of a transistor Q1 which might be a type 2N3906. The base of transistor Q1 is connected to lead 52 which is connected to resistor R12 and to the probe tip contact 13. A lead 53 is connected to the collector of transistor Q1 and to a capacitor C3 which might be a 0.1 microfarad which has its other side connected to ground. A resistor R2 which might be 680K is connected in parallel with the capacitor C3. Integrated circuit U1B is connected to lead 53 and receives a second input on lead 54 from the junction point between resistors RP2A and RP1A which are connected in series between voltage VCC and ground. Lead 54 is also connected to an integrated circuit U1C. The output of integrated circuit U1B is connected to lead 56 which is connected to ground through a capacitor C1 which might be 0.01 microfarad. Lead 56 is also connected to an input of an integrated circuit U1A. A resistor R1 is connected to lead 56 and has its other side connected to a lead 57 which is connected to the output of the integrated circuit U1A and also to the input of a speaker 46. Voltage $V_{CC}$ is connected to a light emitting diode 41 which has its other side connected to resistor R3 which might be 680K and which is connected to the speaker 46 as shown. A resistor RP2D which might be 220K is connected from lead 57 to lead 58. A resistor RP2B is connected from voltage $V_{CC}$ to lead 58 and is in series with the resistor RP2C which has its other side connected to ground. The resistors RP2B and RP2C may each be 220K resistors.

Voltage $V_{CC}$ is connected to a resistor RP1C which is in series to ground through a resistor RP1B and these resistors both may be 220K. A lead 59 is connected between the junction point of the resistors RP1C and RP1B and an input of an integrated circuit U1D. A lead 61 is connected to the input of integrated circuit U1D and a capacitor C4 is connected between lead 61 and ground. Capacitor C4 might be 0.1 microfarad. A resistor R4 is connected between lead 61 and switch 42 which is moveable between an open circuit slow pulse position and a closed fast pulse position which engages lead 63. Resistor R4 might be 2.7 megohms. A resistor R5 is connected between lead 61 and 63 and may be 2.7 megohms. A resistor R6 is connected from lead 61 to a diode D2 which might be a type 1N914 which has its other side connected to lead 63. Resistor R6 may be 2.7 megohms. The output of integrated circuit U1D is connected to lead 63 and a resistor RP1D is connected between the input and output of the integrated circuit U1D and might be 220K ohms. The lead 63 is connected to the input of an integrated circuit U1C. A resistor R7 which might be 4.7kohms is connected between voltage $V_{CC}$ and the input to the integrated circuit U1C. The output lead 64 of integrated circuit U1C is connected to resistors R8 and R9. Resistor R8 may be 1.1k and resistor R9 may be 11k. High/low switch 44 is moveable to engage contacts 66 and 67 which are, respectively, connected to the resistors R8 and R9. Switch 44 is connected to lead 68 which is connected to the emitter of transistor Q2 which might be a type 2N3904. The base of transistor Q2 is connected to one side of a resistor R10 which might be 3.3kohm resistor which has its other side connected to reference voltage $V_{CC}$. The base of transistor Q2 is also connected through a Zener diode D3 to ground. The Zener diode D3 might be a type 1N5230. The collector of transistor Q2 is connected to a capacitor C5 which might be 1.0 microfarad and to resistor R11 which might be 680k which is connected in parallel with the capacitor C5 and to lead 69 which is connected to return contact 17. All of the integrated circuits U1A, U1B, U1C and U1D may be type LM339.

In use, the surgeon connects the monitoring electrode 15 to the patient such that the pad 24 makes good electrical contact with the skin of the patient. The on/off switch 43 is moved to the on position so it engages the lead 51 to apply voltage from the battery to the circuit. As the surgeon dissects, he uses the probe 12 with the electrode 13 to contact tissue so as to locate nerves for example. The purpose of which is to both locate the nerve and to demonstrate the integrity of the nerve by probing with electrode 13. The high current setting is used for direct muscle stimulation. The switch 44 allows different current values to be applied to the probe so that different current values will flow between the tip 13 and contact 17. The switch 42 allows a fast pulse to be applied between the probe 13 and the contact 17, when the switch engages lead 63 so as to place resistor R4 in circuit. The surgeon may also actuate switch 42 to open it to apply a slower pulse between the tip 13 and contact 17.

The light 41 and the speaker 46 provide visual and aural feedback to the surgeon to indicate that the device is operating properly. The switch 44 allows pulse current such as 250 microsecond width pulses at two amplitude settings of 300 micro-amps and 3 milli-amps to be selected. The amplitude of current pulses remain constant over a range of resistances. The switch 42 allows two pulse rate settings of five pulses per second or ten pulses per second to be selected. The probe tip is insulated to prevent contact except at the extreme end of the tip wherein the probe 13 extends from the insulated shield 12.

The invention minimizes the possibility of any neuropraxia due to overstimulation of the nerve.

Although the invention has been described with respect to preferred embodiments, it is not to be so limited as changes and modifications can be made therein which are within the full intended scope as defined by the appended claims.

I claim as my invention:

1. A surgical nerve stimulator and locator which does not induce neuropraxia adapted to be used on a patient comprising, a handpiece, a first electrical lead connected to said handpiece and connectible to the patient's body, a second electrical lead connected to said handpiece and connectible to the patient's body to locate and stimulate nerves, a D.C. voltage source in said handpiece, a pulsed current source in said handpiece connected to said first and second electrical leads and to said voltage source, and a first two position switch connected to said pulsed current source and in a first position causing a pulse to be generated by said pulsed current source having a first pulse repetition rate and in a second position causing a pulse to be generated by said pulsed current source having a second pulse repetition rate, including a second two position switch connected to said pulsed current source and in a first position causing said pulsed current source to generate current pulses having a first amplitude and in a second position causing said pulsed current source to generate current pulses having a second amplitude, wherein said second electrical lead is enclosed by insulation material except at its end remote from said hand piece, including an indicator connected to said first and second electrical leads to indicate when current flows between them through the patient's body, and including a loudspeaker connected to said first and second electrical leads to aurally indicate when current flows between them through the patient's body.

2. A surgical nerve stimulator and locator according to claim 1 including an electrocardiogram electrode connected to said first lead at its end remote from said handpiece connectable to the patient's body.

* * * * *